(12) United States Patent
Onaga

(10) Patent No.: US 9,214,299 B2
(45) Date of Patent: Dec. 15, 2015

(54) OPERATION COMMAND TRANSMITTING DEVICE

(71) Applicant: OLYMPUS CORPORATION, Tokyo (JP)

(72) Inventor: Takeshi Onaga, Kodaira (JP)

(73) Assignee: OLYMPUS CORPORATION, Tokyo (JP)

( * ) Notice: Subject to any disclaimer, the term of this patent is extended or adjusted under 35 U.S.C. 154(b) by 8 days.

(21) Appl. No.: 14/145,389

(22) Filed: Dec. 31, 2013

(65) Prior Publication Data
US 2014/0190806 A1 Jul. 10, 2014

Related U.S. Application Data

(63) Continuation of application No. PCT/JP2013/051878, filed on Jan. 29, 2013.

(60) Provisional application No. 61/604,191, filed on Feb. 28, 2012.

(51) Int. Cl.
*H01H 25/00* (2006.01)
*H01H 13/08* (2006.01)
(Continued)

(52) U.S. Cl.
CPC ........ *H01H 13/08* (2013.01); *A61B 17/320092* (2013.01); *H01H 25/06* (2013.01); *A61B 18/1445* (2013.01); *A61B 2017/00367* (2013.01); *A61B 2018/00952* (2013.01)

(58) Field of Classification Search
CPC ........... H01H 25/00; H01H 3/06; H01H 3/12; H01H 13/00; H01H 13/50; H01H 21/22; H01H 23/00; H01H 2003/12; H01H 2009/0088; H01H 2019/00; H01H 2221/012; H01H 2221/01; H01H 2231/01; H01H 2231/002; H01H 2231/008
USPC .......... 200/6 A, 6 R, 4, 37, 19.18–19.19, 547, 200/529, 553, 252, 321, 336, 339, 17 R, 200/50.34, 50.35, 329
See application file for complete search history.

(56) References Cited

U.S. PATENT DOCUMENTS 3,772,484 A * 11/1973 Roeser .............................. 200/4
4,563,549 A    1/1986 Lycan
(Continued)

FOREIGN PATENT DOCUMENTS

GB      1114630 A       5/1968
JP    A-2000-353455   12/2000
(Continued)

OTHER PUBLICATIONS

International Search Report issued in International Patent Application No. PCT/JP2013/051878 mailed Mar. 12, 2013.
(Continued)

*Primary Examiner* — Edwin A. Leon
*Assistant Examiner* — Anthony R. Jimenez
(74) *Attorney, Agent, or Firm* — Oliff PLC

(57) ABSTRACT

An operation command transmitting device includes a coupling portion coupling a bar portion to a housing so that the bar portion is movable relative to the housing along a central axis and the bar portion is allowed to be tilted around a supporting axis passing through the bar portion, and an abutment portion with which the bar portion comes into abutment when the bar portion is tilted from an untilted neutral condition. The operation command transmitting device includes an axis defining portion defining the supporting axis so that a position of the supporting axis relative to the housing does not change regardless of a tilting of the bar portion and a movement of the bar portion along the central axis.

7 Claims, 12 Drawing Sheets

(51) Int. Cl.
*H01H 25/06* (2006.01)
*A61B 17/32* (2006.01)
*A61B 17/00* (2006.01)
*A61B 18/00* (2006.01)
*A61B 18/14* (2006.01)

(56) References Cited

U.S. PATENT DOCUMENTS 6,344,618 B1    2/2002  Sato
7,199,314 B2 *  4/2007  Huang et al. .................. 200/6 A
2006/0060365 A1 * 3/2006  Kunz .............................. 173/48

2007/0170046 A1    7/2007  Ito

FOREIGN PATENT DOCUMENTS

JP    A-2007-199971    8/2007
JP    A-2008-305604    12/2008
JP    B2-4763093       8/2011

OTHER PUBLICATIONS

Jul. 20, 2015 Search Report issued in European Patent Application No. 13755683.3.

* cited by examiner

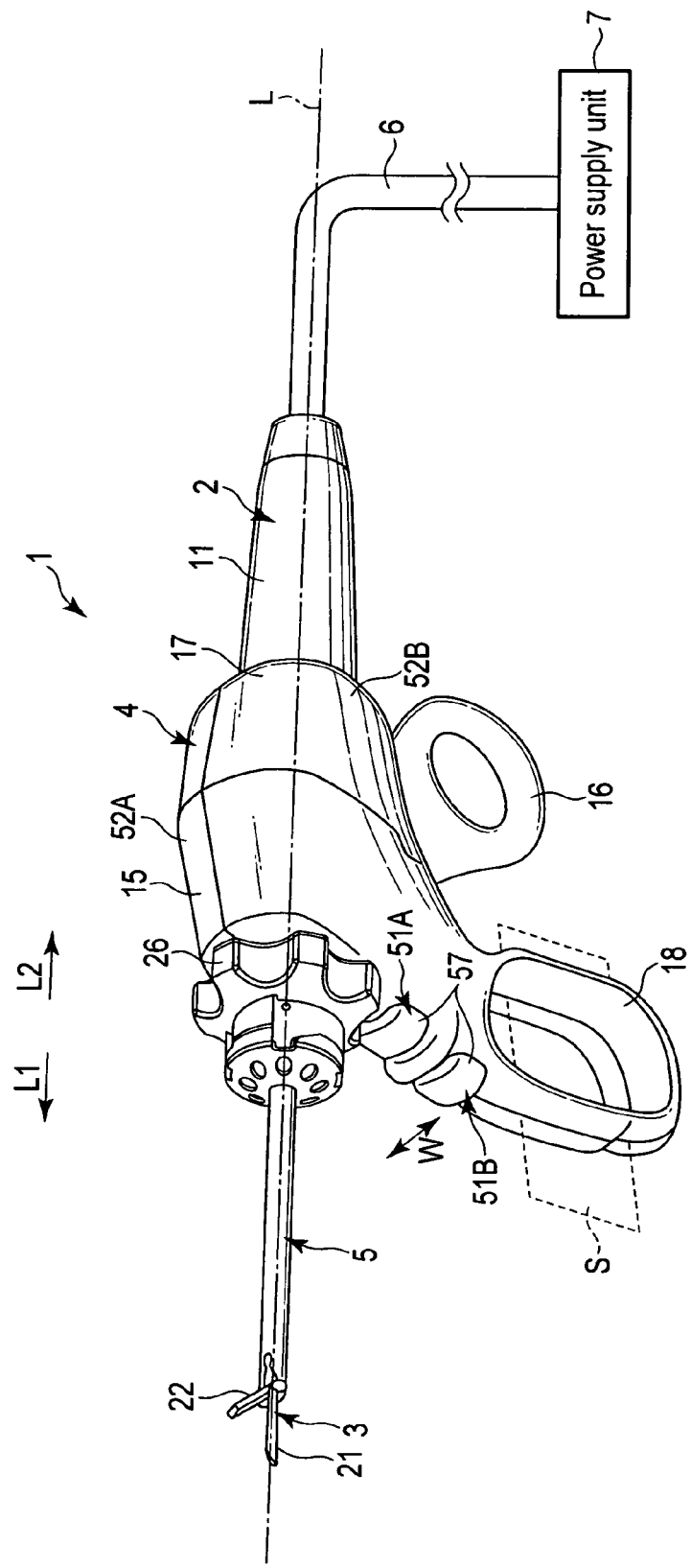
F I G. 1

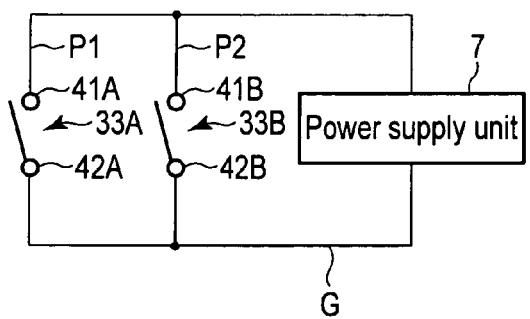
F I G. 4
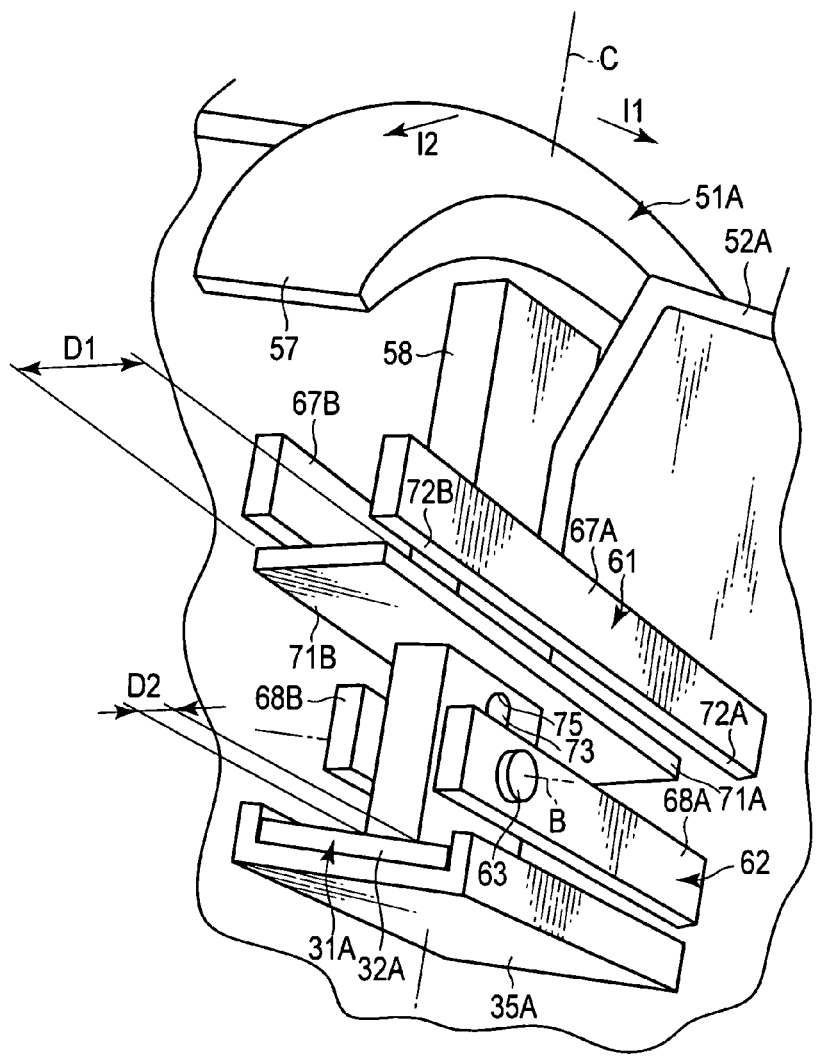
F I G. 5

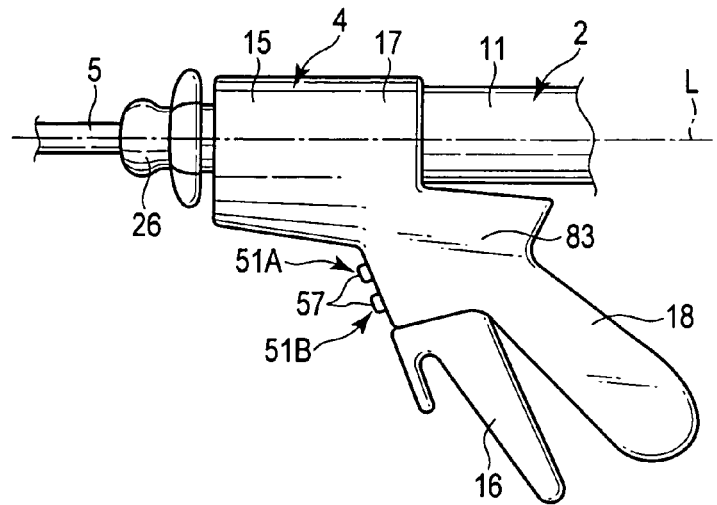
F I G. 14
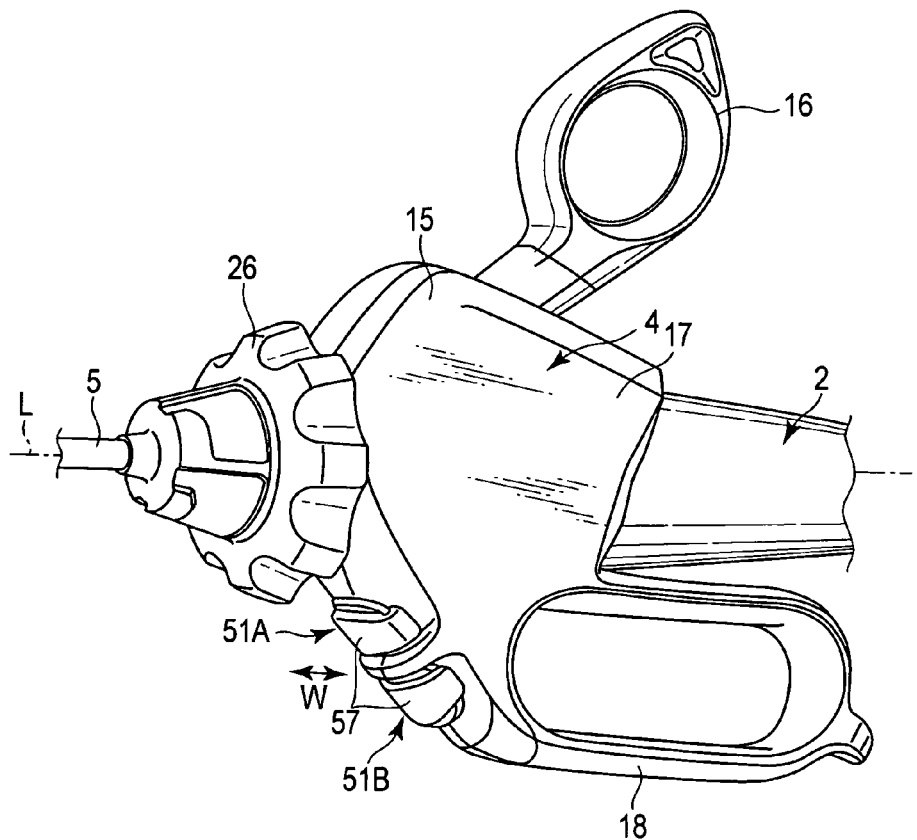
F I G. 15

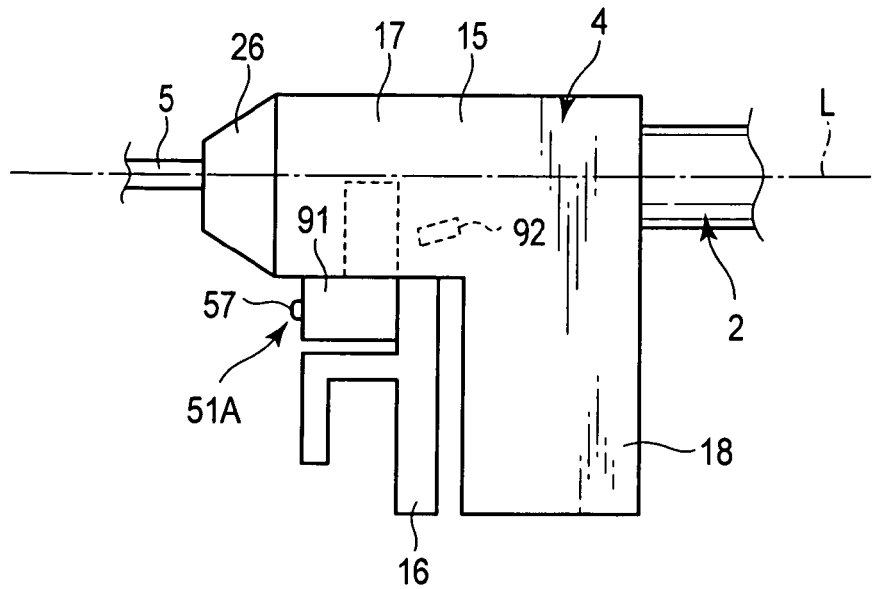
F I G. 19
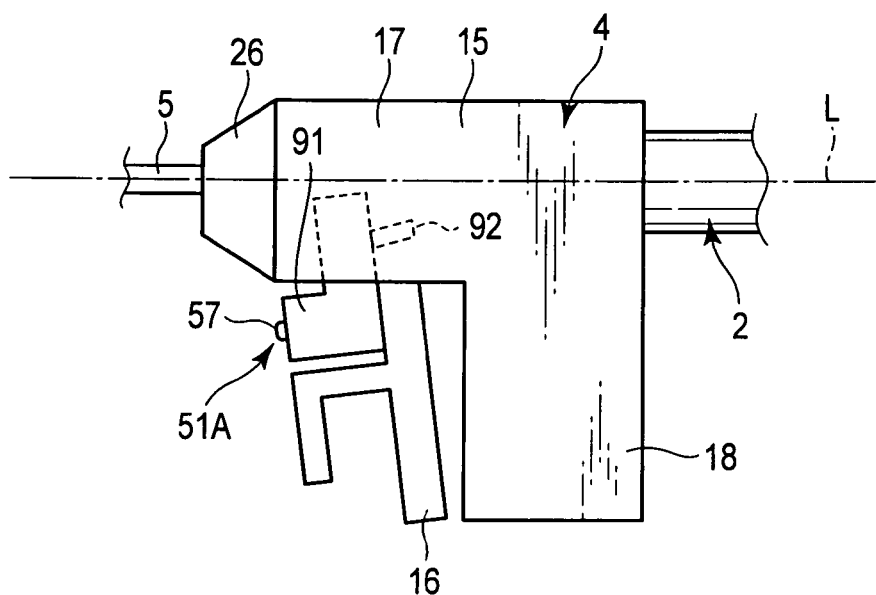
F I G. 20

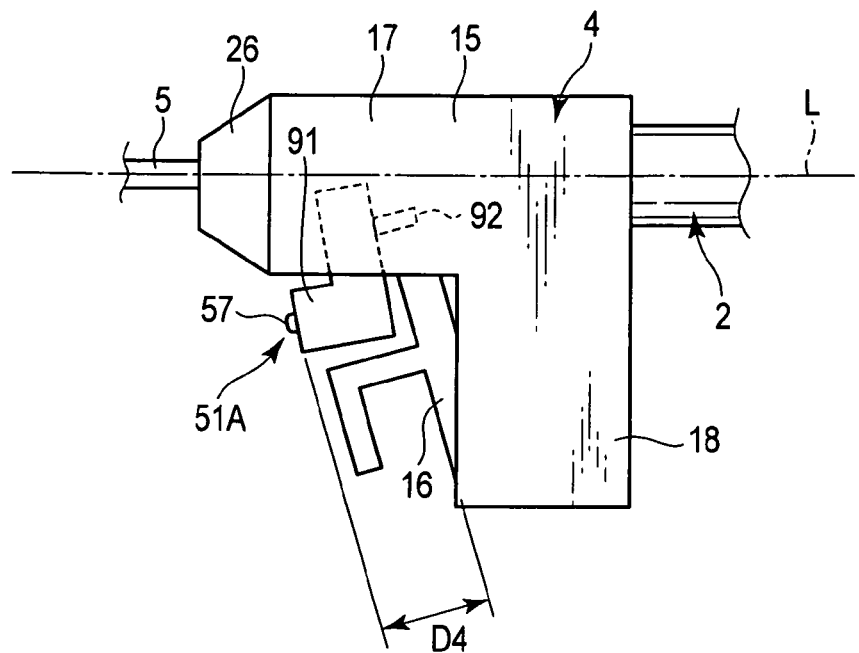
F I G. 21
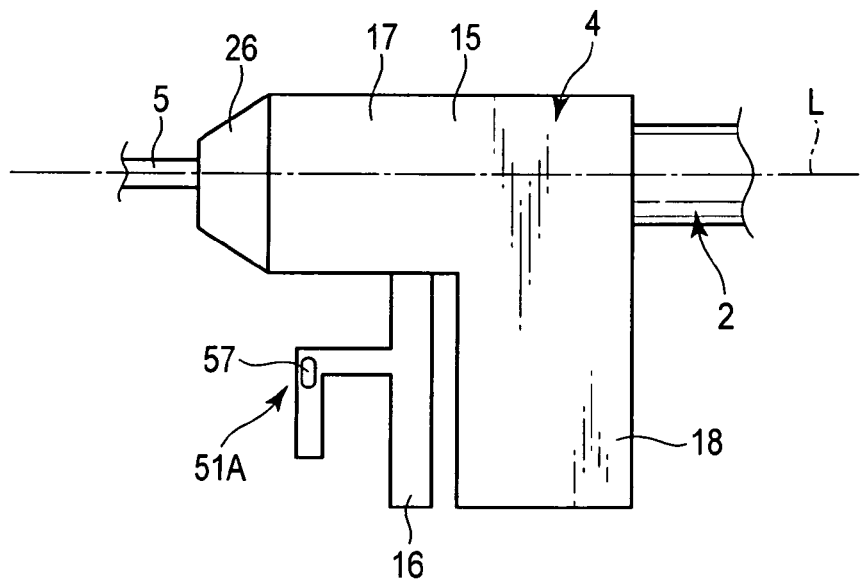
F I G. 22

OPERATION COMMAND TRANSMITTING DEVICE

CROSS-REFERENCE TO RELATED APPLICATIONS

This is a Continuation application of PCT Application No. PCT/JP2013/051878, filed Jan. 29, 2013 and based upon and claiming the benefit of priority from prior U.S. Provisional Application No. 61/604,191, filed Feb. 28, 2012, the entire contents of which are incorporated herein by reference.

BACKGROUND OF THE INVENTION

1. Field of the Invention

The present invention relates to an operation command transmitting device which is configured to transmit a signal indicating an operation command when a switch contact is turned on by the application of press force to a pressure receiving portion of an on-or-off switching member.

2. Description of the Related Art

Japanese Patent No. 4763093 has disclosed an operation command transmitting device including a transmitting unit which is configured to transmit a signal indicating an operation command when a switch contact is turned on. This operation command transmitting device is provided with an on-or-off switching member which includes a pressure receiving portion pressably provided outside a housing, and a bar portion extending from the pressure receiving portion toward the switch contact along a central axis. In response to the application of press force to the pressure receiving portion, a switch pressing portion of the bar portion presses the switch contact, and turns on the switch contact. The on-or-off switching member is supported by a support portion of the housing so that the central axis can be tilted in tilting directions perpendicular to the central axis from a neutral condition in which the central axis is perpendicular to a substrate of the transmitting unit. The support portion pinches the bar portion from both sides in the tilting directions. A space is formed between the bar portion and the support portion, and the provision of the space permits the on-or-off switching member to be tilted from the neutral condition in one of the tilting directions. The on-or-off switching member is provided with protrusions each projecting from the bar portion in one of the tilting directions. The housing is provided with abutment portions which are located closer to the pressure receiving portion than the protrusions in directions parallel to the central axis, and the corresponding one protrusion abuts each of the abutment portions in the neutral condition.

When press force is applied to the pressure receiving portion at a position located apart from the central axis toward one of the tilting directions, the on-or-off switching member is tilted in one of the tilting directions. In this case, the on-or-off switching member is tilted about (around) an abutment position between one of the protrusions of the on-or-off switching member and the corresponding abutment portion of the housing. In response to the inclining of the on-or-off switching member, the switch pressing portion of the bar portion presses the switch contact, and turns on the switch contact.

BRIEF SUMMARY OF THE INVENTION

According to one aspect of the invention, an operation command transmitting device includes that: a graspable housing; a switch contact including a fixed electric contact provided inside the housing to be fixed with respect to the housing; a pressure receiving portion pressably provided outside the housing; a bar portion extending from the pressure receiving portion toward the switch contact along a central axis; a switch pressing portion which is provided in a part of the bar portion on an opposite side with respect to the pressure receiving portion, and which is configured to press the switch contact when press force is applied to the pressure receiving portion; a coupling portion which couples the bar portion to the housing so that the bar portion is movable relative to the housing along the central axis and so that the bar portion is allowed to be tilted around a supporting axis which passes through the bar portion; an abutment portion provided integrally with the housing or provided to be fixed with respect to the housing, the bar portion being configured to come into abutment with the abutment portion when the bar portion is tilted from an untilted neutral condition; and an axis defining portion which defines the supporting axis so that a position of the supporting axis relative to the housing does not change regardless of a tilting of the bar portion and a movement of the bar portion along the central axis.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic perspective view showing an ultrasonic treatment device according to a first embodiment of the present invention;

FIG. 4 is a circuit diagram showing the electric connection between the transmitting unit and the power supply unit according to the first embodiment;

FIG. 5 is a schematic perspective view showing the configurations of one transmitting unit, and an on-or-off switching member corresponding to the transmitting unit in the neutral condition according to the first embodiment;

FIG. 14 is a schematic diagram showing the configuration of the handle unit according to a third modification;

FIG. 15 is a schematic perspective view showing the configuration of the handle unit according to a fourth modification;

FIG. 19 is a schematic diagram showing the configuration of the handle unit according to a second reference example when the movable handle is maximally opened;

FIG. 20 is a schematic diagram showing the configuration of the handle unit according to the second reference example when a movable member is in abutment with a stopper;

FIG. 21 is a schematic diagram showing the configuration of the handle unit according to the second reference example when the movable handle is maximally closed; and FIG. 22 is a schematic diagram showing the configuration of the handle unit according to a third reference example.

DETAILED DESCRIPTION OF THE INVENTION

First Embodiment

Figure 2:
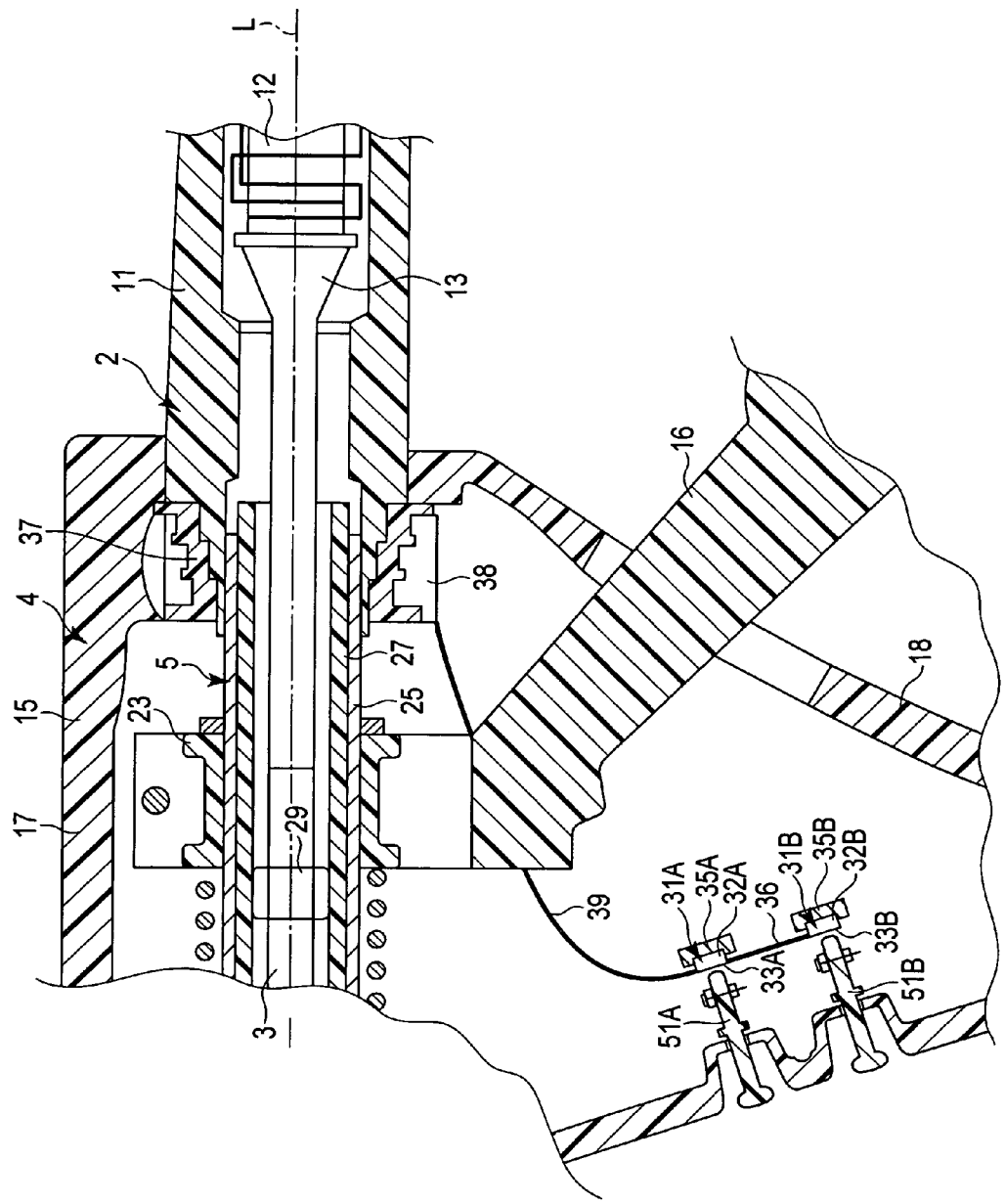
FIG. 2 is a schematic sectional view showing configurations of an inside of a handle unit and an inside of a vibrator unit according to the first embodiment.

A first embodiment of the present invention is described with reference to FIG. 1 to FIG. 11. FIG. 1 is a diagram showing an ultrasonic treatment device 1 according to the present embodiment. As shown in FIG. 1, the ultrasonic treatment device 1 has a longitudinal axis L. Here, one of two directions parallel to the longitudinal axis L is a distal direction (direction of an arrow L1 in FIG. 1), and the direction opposite to the distal direction is a proximal direction (direction of an arrow L2 in FIG.

The ultrasonic treatment apparatus 1 includes a vibrator unit 2, a probe 3, a handle unit 4 which is an operation command transmitting device, and a sheath 5. The vibrator unit 2 includes a vibrator case 11. One end of a cable 6 is connected to a proximal portion of the vibrator case 11. The other end of the cable 6 is connected to a power supply unit 7.

FIG. 2 is a diagram showing configurations of an inside of the handle unit 4 and an inside of the vibrator unit 2. As shown in FIG. 2, an ultrasonic vibrator 12 including a piezoelectric element which is configured to convert a current to an ultrasonic vibration is provided in the vibrator case 11. The ultrasonic transducer 12 generates the ultrasonic vibration when supplied with a current from the power supply unit 7 via an electric signal line (not shown) provided inside the cable 6. A columnar horn 13 which is configured to increase the amplitude of the ultrasonic vibration is coupled to the distal-direction side of the ultrasonic oscillator 12. The horn 13 is supported by the transducer case 11.

As shown in FIG. 1, the handle unit 4 which is the operation command transmitting device includes a housing 15 which can be grasped by a surgeon. The housing 15 includes a cylindrical case 17 extending along the longitudinal axis L, and a fixed handle 18 extending from the cylindrical case 17 substantially perpendicularly to the longitudinal axis L. The housing 15 also includes a movable handle 16 which is rotatably attached to the cylindrical case 17. When the movable handle 16 rotates relative to the cylindrical case 17, the movable handle 16 is opened or closed relative to the fixed handle 18. That is, the movable handle 16 is provided to be openable and closable relative to the fixed handle 18. The movable handle 16 is located to the proximal-direction side of the fixed handle 18. The opening-and-closing directions of the movable handle 16 are substantially parallel to the longitudinal axis L.

As shown in FIG. 2, the transducer unit 2 is coupled to the cylindrical case 17 from the proximal-direction side, and the sheath 5 is coupled to the cylindrical case 17 from the distal-direction side. The probe 3 is inserted into the cylindrical case 17 from the distal-direction side, and the probe 3 is inserted through the sheath 5. A proximal end of the probe 3 is connected to a distal end of the horn 13 inside the cylindrical case 17. Moreover, the sheath 5 is coupled to the vibrator case 11 inside the cylindrical case 17.

As shown in FIG. 1, a probe treatment section 21 is provided to a distal portion of the probe 3. A jaw 22 is rotatably attached to a distal portion of the sheath 5. The jaw 22 is openable and closable relative to the probe treatment section 21 of the probe 3. The jaw 22 is opened or closed relative to the probe treatment section 21 by the movable handle 16. As shown in FIG. 2, the movable handle 16 is attached to a slider portion 23 of the sheath 5. The slider portion 23 is provided on an outer peripheral portion of a movable cylindrical member 25. When the movable handle 16 is opened or closed relative to the fixed handle 18, the slider portion 23 and the movable cylindrical member 25 move along the longitudinal axis L. When the movable cylindrical member 25 moves, a movable pipe (not shown) of the sheath 5 moves along the longitudinal axis L, and the jaw 22 is opened or closed.

As shown in FIG. 1, the handle unit 4 includes a rotational operation knob 26 which is coupled to the distal-direction side of the cylindrical case 17. The rotational operation knob 26 is coupled to the cylindrical case 17 rotatably in directions around the longitudinal axis. As shown in FIG. 2, a connection cylindrical member 27 is provided to an inner-peripheral-direction side of the movable cylindrical member 25 of the sheath 5. A proximal portion of the connection cylindrical member 27 is coupled to the vibrator case 11. The rotational operation knob 26 is also coupled to the connection cylindrical member 27 and the movable cylindrical member 25 of the sheath 5. Therefore, rotational drive force from the rotational operation knob 26, can be transmitted to the connection cylindrical member 27 and the movable cylindrical member 25 of the sheath 5.

An elastic member 29 is fixed between an outer circumferential portion of the probe 3 and the connection cylindrical member 27. The elastic member 29 is pressed toward the inner peripheral direction by an inner peripheral portion of the connection cylindrical member 27, and is contracted. The probe 3 is fixed to the connection cylindrical member 27 by the contraction of the elastic member 29, and the probe 3 is coupled to the sheath 5 by the connection cylindrical member 27 and the elastic member 29. Consequently, the rotational drive force from the rotational operation knob 26 can be transmitted to the probe 3 via the connection cylindrical member 27 and the elastic member 29. According to the configuration described above, the probe 3, the sheath 5, the jaw 22, and the vibrator unit 2 are rotatable relative to the cylindrical case 17 together with the rotational operation knob 26.

Transmitting units 31 (31A and 31B) are provided inside the fixed handle 18 of the housing 15. Each of the transmitting units 31A and 31B includes a substrate 32 (32A or 32B), and a switch contact 33 (33A or 33B) provided on the corresponding substrate 32A or 32B. Substrate fixing portions 35 (35A and 35B) are provided inside the fixed handle 18. A corresponding substrate 32A or 32B is fixed to each of the substrate fixing portions 35A and 35B. The substrates 32A and 32B are connected to each other via a flexible substrate 36.

An electric connection ring 37 is provided inside the cylindrical case 17 of the housing 15 so that the electric connection ring 37 is fixed to the housing 15. When the vibrator case 11 is coupled to the sheath 5 (movable cylindrical member 25), the outer circumferential portion of a distal portion of the oscillator case 11 is in contact with the electric connection ring 37. The vibrator case 11 and the sheath 5 are rotatable together relative to the electric connection ring 37 in the directions around the longitudinal axis. A substrate 38 is fixed to the electric connection ring 37. The substrate 32 and the substrate 38 are connected to each other via a flexible substrate 39.

Figure 3:
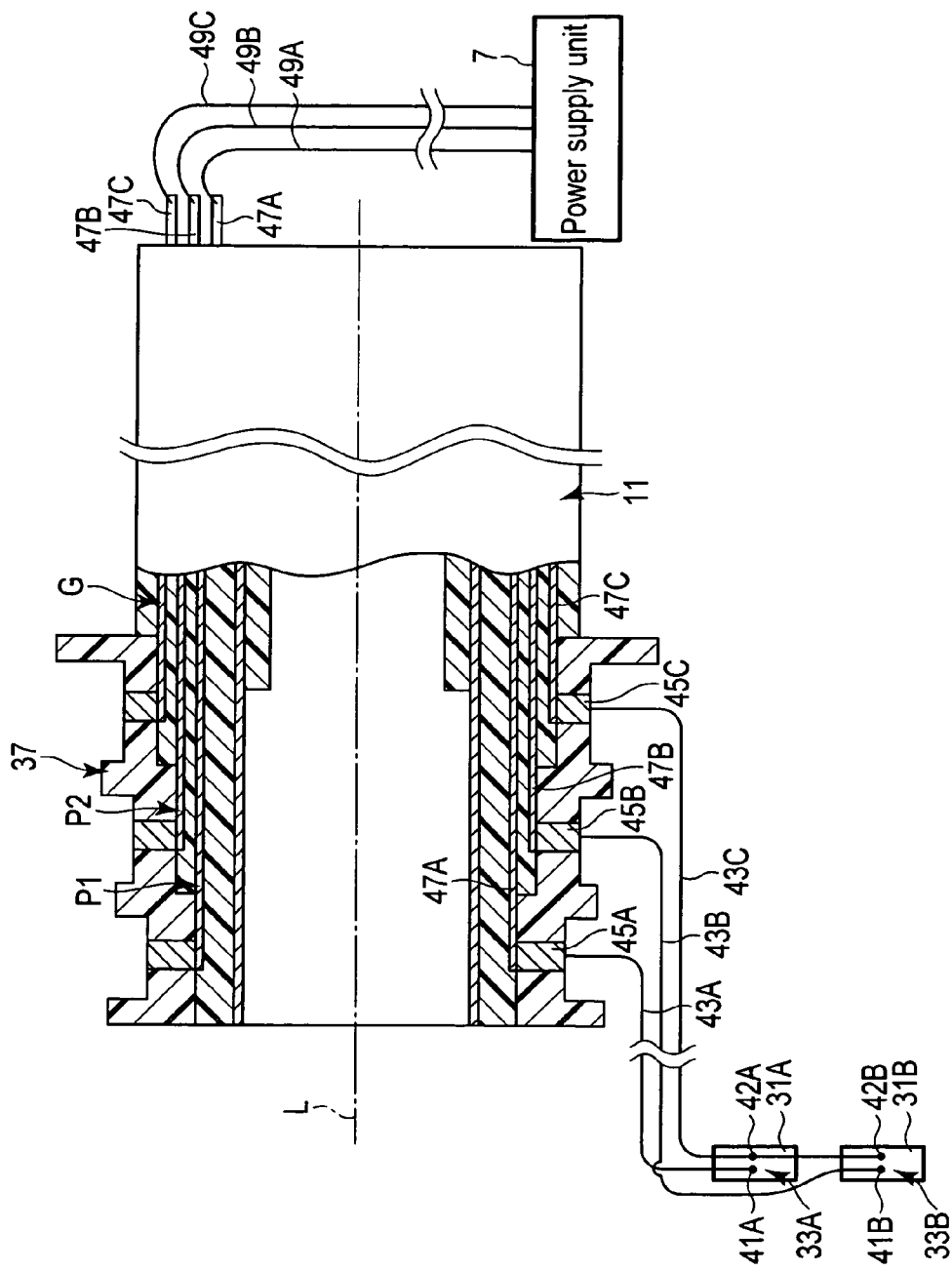
FIG. 3 is a schematic diagram showing electric connection between a transmitting unit and a power supply unit according to the first embodiment.

FIG. 3 and FIG. 4 are diagrams showing electric connection between the transmitting units 31A and 31B and the power supply unit 7. As shown in FIG. 3 and FIG. 4, the switch contact 33A of the transmitting unit 31A includes a first electric contact 41A and a second electric contact 42A. Similarly, the switch contact 33B of the transmitting unit 31B includes a first electric contact 41B and a second electric contact 42B. Three electric signal lines 43A to 43C are provided on the flexible substrate 39. The electric signal line 43A is electrically connected to the first electric contact 41A of the switch contact 33A via an electric circuit on the substrate 32A. The electric signal line 43B is electrically connected to the first electric contact 41B of the switch contact 33B via the electric circuit on the substrate 32A, an electric circuit on the flexible substrate 36, and an electric circuit on the substrate 32B. The electric signal line 43C is electrically connected to the second electric contact 42A of the switch contact 33A and the second electric contact 42B of the switch contact 33B via the electric circuit on the substrate 32A, the electric circuit on the flexible substrate 36, and the electric circuit on the substrate 32B. The electric signal line 43C is a common line shared as a ground line of the switch contacts 33A and 33B.

As shown in FIG. 3, the electric connection ring 37 includes an electric connection portion 45A, an electric connection portion 45B, and an electric connection portion 45C. The electric connection portions 45A to 45C are electrically insulated from one another. The electric signal line 43A is connected to the electric connection portion 45A via an electric circuit on the substrate 38. The electric signal line 43B is connected to the electric connection portion 45B via the electric circuit on the substrate 38. The electric signal line 43C is connected to the electric connection portion 45C via the electric circuit on the substrate 38.

The vibrator case 11 includes an electric conducting portion 47A, an electric conducting portion 47B, and an electric conducting portion 47C. The electric conducting portions 47A to 47C extend along the longitudinal axis L, and are electrically insulated from one another. When the vibrator case 11 is coupled to the movable cylindrical member 25 (sheath 5), a distal portion of the electric conducting portion 47A alone is in electric contact with the electric connection portion 45A of the electric connection ring 37. Similarly, a distal portion of the electric conducting portion 47B alone is in electric contact with the electric connection portion 45B of the electric connection ring 37. A distal portion of the electric conducting portion 47C alone is in electric contact with the electric connection portion 45C of the electric connection ring 37.

One end of an electric signal line 49A is connected to a proximal portion of the electric conducting portion 47A. One end of an electric signal line 49B is connected to a proximal portion of the electric conducting portion 47B. One end of an electric signal line 49C is connected to a proximal portion of the electric conducting portion 47C. The other ends of the electric signal lines 49A to 49C are connected to the power supply unit 7 through an inside of the cable 6.

As described above, a first electric signal path P1 is formed from the first electric contact 41A of the switch contact 33A to the power supply unit 7 through the electric signal line 43A, the electric connection portion 45A, the electric conducting portion 47A, and the electric signal line 49A. A second electric signal path P2 is formed from the first electric contact 41B of the switch contact 33B to the power supply unit 7 through the electric signal line 43B, the electric connection portion 45B, the electric conducting portion 47B, and the electric signal line 49B. Moreover, a ground path G is formed from the second electric contact 42A of the switch contact 33A and the second electric contact 42B of the switch contact 33B to the power supply unit 7 through the electric signal line 43C, the electric connection portion 45C, the electric conducting portion 47C, and the electric signal line 49C.

As shown in FIG. 4, when the first electric contact 41A contacts the second electric contact 42A in the switch contact 33A, the switch contact 33A is turned on. As a result, the first electric signal path P1 is electrically connected to the ground path G in the switch contact 33A. A signal indicating an operation command is transmitted to the power supply unit 7 from the transmitting unit 31A. When the signal is input to the power supply unit 7 from the transmitting unit 31A, for example, an ultrasonic generating current is output to the ultrasonic vibrator 12 from the power supply unit 7. Thus, the ultrasonic vibration generated in the ultrasonic vibrator 12 is transmitted to the probe treatment section 21 via the horn 13 and the probe 3.

When the first electric contact 41B contacts the second electric contact 42B in the switch contact 33B, the switch contact 33B is turned on. As a result, the second electric signal path P2 is electrically connected to the ground path G in the switch contact 33B. A signal indicating an operation command is then transmitted to the power supply unit 7 from the transmitting unit 31B. When the signal is input to the power supply unit 7 from the transmitting unit 31B, for example, a high-frequency current is transmitted to the probe treatment section 21 from the power supply unit 7 via an electric wiring line (not shown) provided inside the cable 6, the ultrasonic vibrator 12, the horn 13, and the probe 3. A high-frequency current is also transmitted to the jaw 22 via the electric wiring line (not shown) provided inside the cable 6, an electric conducting portion (not shown) of the vibrator case 11 different from the electric conducting portions 47A to 47C, and an electric conducting portion (not shown) of the sheath 5.

As shown in FIG. 1, an on-or-off switching member 51A which can turn on and off the switch contact 33A and an on-or-off switching member 51B which can turn on and off the switch contact 33B are installed on the distal-direction side surface of the fixed handle 18. The housing 15 includes a first housing construct 52A, and a second housing construct 52B coupled to the first housing construct 52A. The second housing construct 52B is separable from the first housing construct 52A on a separation surface S. The separation surface S passes through the substrate 32A of the transmitting unit 31A and the substrate 32B of the transmitting unit 31B, and is perpendicular to width directions (directions of arrows W in FIG. 1) of the housing 15. The second housing member 52B is separable from the first housing member 52A parallel to the width directions on the separation surface S.

Figure 6:
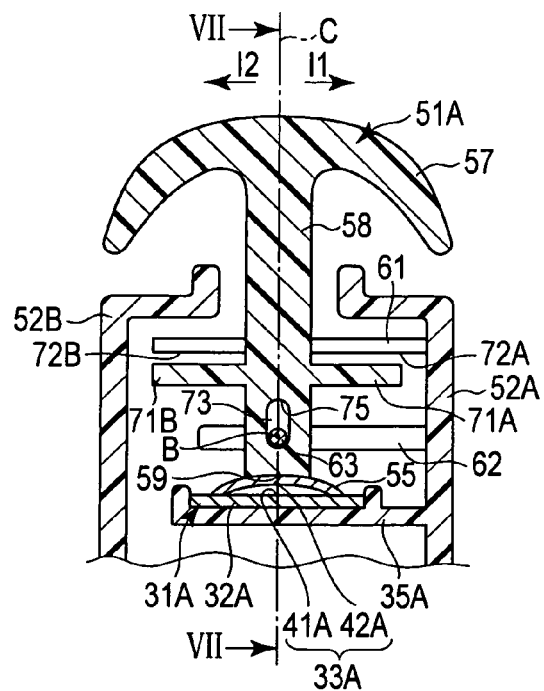
FIG. 6 is a schematic sectional view showing, in a section perpendicular to a supporting axis, the configurations of one transmitting unit, and the on-or-off switching member corresponding to the transmitting unit in the neutral condition according to the first embodiment.
Figure 7:
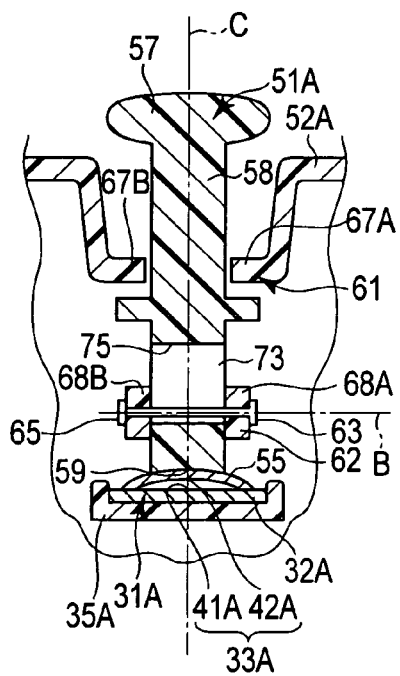
FIG. 7 is a sectional view taken along the line VII-VII of FIG. 6.

FIG. 5 to FIG. 7 are diagrams showing the configurations of the transmitting unit 31A and the switching member 51A. While the configurations and functions of the transmitting unit 31A and the switching member 51A are described below, the configurations and functions of the transmitting unit 31B and the switching member 51B are similar to those of the transmitting unit 31A and the switching member 51A and are therefore not described.

As shown in FIG. 5 to FIG. 7, the transmitting unit 31A is installed on the substrate fixing portion 35A. The substrate fixing portion 35A is provided integrally with the first housing construct 52A of the housing 15, or provided to be fixed to the first housing construct 52A. The substrate 32A of the transmitting unit 31A is fixed to the substrate fixing portion 35A. Therefore, the substrate 32A is provided to be fixed with respect to the first housing member 52A of the housing 15.

On the substrate 32A, the first electric contact 41A of the switch contact 33A is provided to be fixed to the substrate 32A. An electrically conductive metallic dome member 55 is attached to the substrate 32A. The dome member 55 is elastic, and is urged so that the dome member 55 does not contact the first electric contact 41A. The second electric contact 42A of the switch contact 33A is provided to the dome member 55. Therefore, the second electric contact 42A is urged so that the second electric contact 42A does not contact the first electric contact 41A.

The on-or-off switching member 51A has a central axis C. The central axis C passes through the transmitting unit 31A. The on-or-off switching member 51A includes a pressure receiving portion 57 provided outside the housing 15, and a bar portion 58 extending from the pressure receiving portion 57 toward the switch contact 33A along the central axis C. The pressure receiving portion 57 can be pressed by the surgeon. A switch pressing portion 59 is provided to an end portion of the bar portion 58 on a side where the switch contact 33A is located in directions parallel to the central axis C.

When press force is applied to the pressure receiving portion 57 by the surgeon, the switch pressing portion 59 presses the dome member 55 (the switch contact 33A). As a result, the dome member 55 moves toward the first electric contact 41A on the substrate 32A against the urging force, and the second electric contact 42A of the dome member 55 comes into contact with the first electric contact 41A. The switch contact 33A is then turned on.

Support portions 61 and 62 are provided inside the housing 15. The support portions 61 and 62 are provided integrally with the first housing construct 52A of the housing 15, or provided to be fixed to the first housing construct 52A. The support portions 61 and 62 support the on-or-off switching member 51A so that the switch pressing portion 59 does not press the switch contact 33A (the dome member 55) in a neutral condition in which no press force is applied to the pressure receiving portion 57. In the neutral condition, the central axis C of the on-or-off switching member 51A is perpendicular to the substrate 32A of the transmitting unit 31A.

The on-or-off switching member 51A is supported by the support portions 61 and 62 so that the switching member 51A can be tilted from the neutral condition toward a first tilting direction (direction of an arrow I1 in FIG. 5 and FIG. 6) perpendicular to the central axis C and toward a second tilting direction (direction of an I2 in FIG. 5 and FIG. 6) opposite to the first tilting direction. In the present embodiment, the first tilting direction and the second tilting direction correspond to the width directions of the housing 15. Therefore, the first inclining direction and the second inclining direction are perpendicular to the opening-and-closing directions of the movable handle 16. The separation surface S on which the second housing construct 52B is separated from the first housing construct 52A is perpendicular to the first tilting direction and the second tilting direction. The second housing construct 52B is separable from the first housing construct 52A parallel to the first tilting direction and the second tilting direction on the separation surface S. FIG. 5 to FIG. 7 show the neutral condition of the on-or-off switching member 51A.

In the directions parallel to the central axis C, the support portion 62 is located closer to the switch contact 33A than the support portion 61. The substrate fixing portion 35A and the support portions 61 and 62 are provided integrally with the first housing construct 52A, or provided to be fixed to the first housing construct 52A. The substrate fixing portion 35A and the support portions 61 and 62 extend toward the second tilting direction from the inner peripheral portion of the first housing construct 52A. Therefore, when the first housing construct 52A and the second housing construct 52B are separated from each other on the separation surface S, the transmitting unit 31A, the substrate fixing portion 35A, the on-or-off switching member 51A, and the support portions 61 and 62 are separated from the second housing construct 52B together with the first housing construct 52A.

A pin 63 is inserted through the support portion 62 and the bar portion 58 of the close-or-open switching member 51A. The pin 63 is fixed to the support portion 62 by a pin stopper 65. Thus, the pin 63 is fixed to the first housing construct 52A of the housing 15. A supporting axis B is defined by a pin shaft of the pin 63. That is, the pin shaft of the pin 63 is coaxial with the supporting axis B. The supporting axis B is parallel to the substrate 32A. The supporting axis B intersects at right angles with the central axis C in the bar portion 58, and is perpendicular to the first tilting direction and the second tilting direction. That is, the first tilting direction and the second tilting direction is perpendicular to the central axis C and perpendicular to the supporting axis B. In this way, the pin 63 serves as an axis defining portion which defines the supporting axis B. The switching member 51A can be tilted around the supporting axis B from the neutral condition.

The support portion 61 is provided with pinch portions 67A and 67B which pinch the bar portion 58 from both sides in directions parallel to the supporting axis B. Similarly, the support portion 62 is provided with pinch portions 68A and 68B which pinch the bar portion 58 from both sides in the directions parallel to the supporting axis B. Since the bar portion 58 is sandwiched from both sides in the directions parallel to the supporting axis B, the tilting of the on-or-off switching member 51A from the neutral condition in directions different from the first tilting direction and the second tilting direction is regulated. That is, the support portions 61 and 62 serve as a tilting directions regulating portion which is configured to regulate the on-or-off switching member 51A so that the on-or-off switching member 51A can be tilted from the neutral condition in the first tilting direction and the second tilting direction alone.

A first protrusion 71A which projects from the bar portion 58 of the on-or-off switching member 51A toward the first tilting direction, and a second protrusion 71B which projects from the bar portion 58 of the on-or-off switching member 51A toward the second tilting direction are provided inside the housing 15. The first protrusion 71A and the second protrusion 71B are provided integrally with the on-or-off switching member 51A, or provided to be fixed to the on-or-off switching member 51A.

In the directions parallel to the central axis C, the first protrusion 71A and the second protrusion 71B are located closer to the switch contact 33A than the support portion 61, and located closer to the pressure receiving portion 57 than the support portion 62. A dimension D1 of each of the first protrusion 71A and the second protrusion 71B in the directions parallel to the supporting axis B is preferably greater than a dimension D2 of the bar portion 58 in the directions parallel to the supporting axis B. The support portion 61 is provided with a first protrusion abutment portion 72A on which the first protrusion 71A can abut, and a second protrusion abutment portion 72B on which the second protrusion 71B can abut. In the directions parallel to the central axis C, the first protrusion abutment portion 72A and the second protrusion abutment portion 72B are located closer to the pressure receiving portion 57 than the first protrusion 71A and the second protrusion 71B.

A hole portion 73 which passes through the bar portion 58 in the directions parallel to the supporting axis B is formed in the bar portion 58. The hole portion 73 is defined by a hole defining portion 75 in the shape of a long hole along the central axis C. The bar portion 58 of the on-or-off switching member 51A is coupled to the pin 63 by the insertion of the pin 63 through the hole portion 73. Since the hole portion 73 is long-hole-shaped, the hole defining portion 75 is movable relative to the pin 63 along the central axis C, and the on-or-off switching member 51A is movable relative to the pin 63 along the central axis C. That is, the hole defining portion 75 serves as a coupling portion which couples the bar portion 58 of the on-or-off switching member 51A to the pin 63 so that the on-or-off switching member 51A is movable along the central axis C relative to the pin 63 which is the axis defining portion. In the directions parallel to the central axis C, the bar portion 58 is coupled to the pin 63 at a position closer to the switch contact 33A than the first protrusion 71A and the second protrusion 71B.

Figure 8:
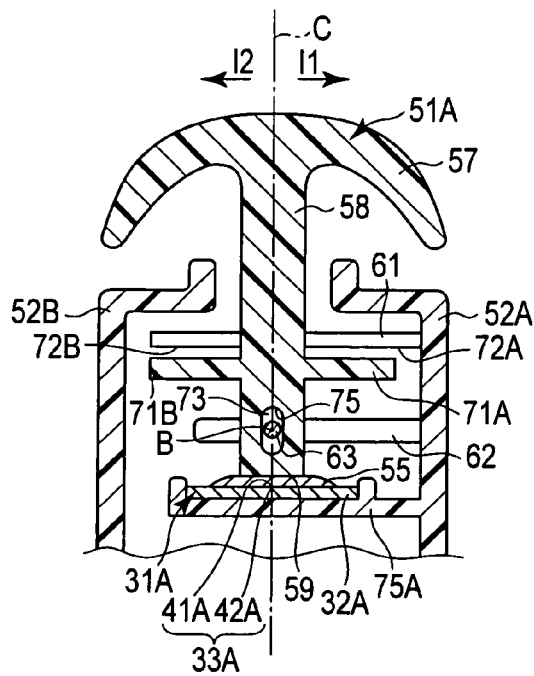
FIG. 8 is a schematic sectional view showing, in the section perpendicular to the supporting axis, the configurations of one transmitting unit, and the on-or-off switching member corresponding to the transmitting unit in a perpendicularly pressed condition according to the first embodiment.

Now, the function of the handle unit 4 which is the operation command transmitting device is described. FIG. 8 is a diagram showing the on-or-off switching member 51A in a perpendicularly pressed condition. When press force is applied to the pressure receiving portion 57 of the on-or-off switching member 51A in the neutral condition (see FIG. 6) in the vicinity of the central axis C, the hole defining portion 75 is moved relative to the pin 63 toward the switch contact 33A along the central axis C by the press force, as shown in FIG. 8. That is, the on-or-off switching member 51A moves toward the switch contact 33A along the central axis C and the perpendicularly pressed condition is caused. In the perpendicularly pressed condition, the central axis C is perpendicular to the substrate 32A of the transmitting unit 31A. The switch contact 33A is pressed by the switch pressing portion 59, and the switch contact 33A is turned on.

In this case, since the switch pressing portion 59 moves toward the switch contact 33A perpendicularly to the substrate 32A from the neutral condition, the switch pressing portion 59 does not move to a great degree in the first tilting direction (direction of an arrow I1 in FIG. 8) and the second tilting direction (direction of an arrow I2 in FIG. 8) from the neutral condition. The switch contact 33A is located at a position where the central axis C passes in the neutral condition. Therefore, the switch pressing portion 59 does not move to a great degree in the first tilting direction and the second tilting direction from the neutral condition, which ensures that the switch contact 33A is pressed by the switch pressing portion 59 in the perpendicularly pressed condition. This ensures that the switch contact 33A is turned on in the perpendicularly pressed condition.

Figure 9:
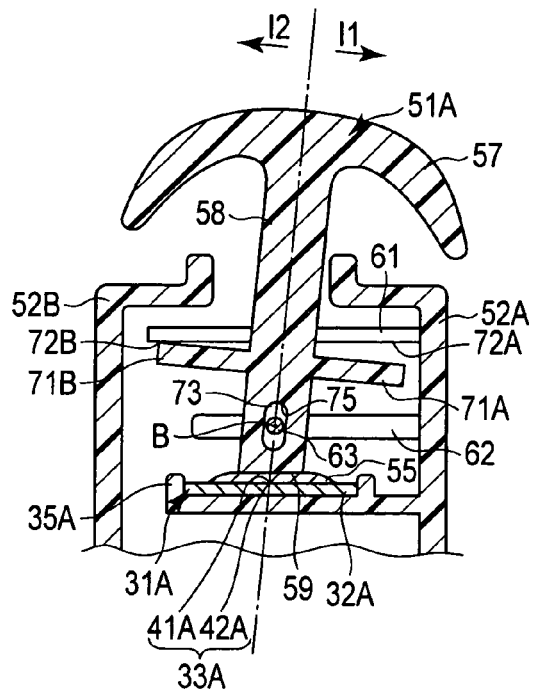
FIG. 9 is a schematic sectional view showing, in the section perpendicular to the supporting axis, the configurations of one transmitting unit, and the on-or-off switching member corresponding to the transmitting unit in a first tiltedly pressed condition according to the first embodiment.
Figure 10:
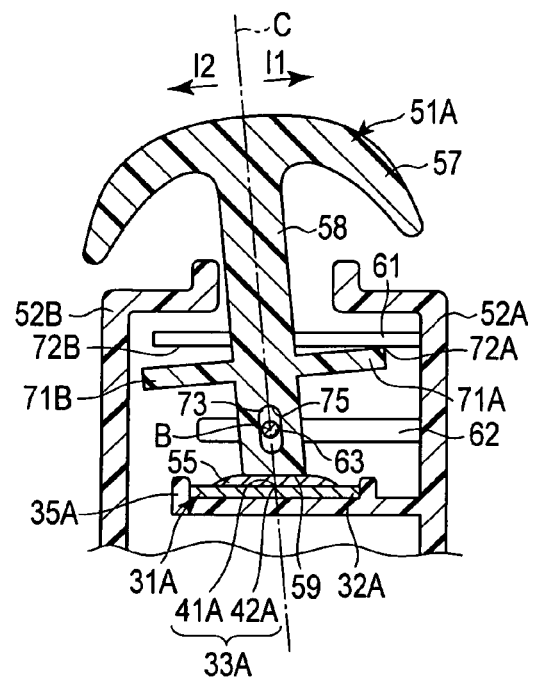
FIG. 10 is a schematic sectional view showing, in the section perpendicular to the supporting axis, the configurations of one transmitting unit, and the on-or-off switching member corresponding to the transmitting unit in a second tiltedly pressed condition according to the first embodiment.

FIG. 9 is a diagram showing the on-or-off switching member 51A in a first tiltedly pressed condition. FIG. 10 is a diagram showing the on-or-off switching member 51A in a second tiltedly pressed condition. When press force is applied to the pressure receiving portion 57 of the switching member 51A in the neutral condition (see FIG. 6) at a position located apart from the central axis C toward the first inclining direction (direction of an arrow I1 in FIG. 9 and FIG. 10) or the second inclining direction (direction of an arrow I2 in FIG. 9 and FIG. 10), the on-or-off switching member 51A is inclined from the neutral condition by the press force. The switching member 51A is tilted toward the first tilting direction or the second tilting direction around the supporting axis B that perpendicularly intersects with the central axis C in the bar portion 58. In this case, the tilting of the on-or-off switching member 51A from the neutral condition in directions different from the first tilting direction and the second tilting direction is regulated by the pinch portions 67A and 67B of the support portion 61 and the pinch portions 68A and 68B of the support portion 62. Thus, the on-or-off switching member 51A is not inclined in the directions different from the first tilting direction and the second tilting direction, and the on-or-off switching member 51A is properly tilted toward the first tilting direction or the second tilting direction from the neutral condition.

When the close-or-open switching member 51A is tilted toward the first tilting direction from the neutral condition, the on-or-off switching member 51A is brought into a first tiltedly pressed condition as shown in FIG. 9. In the first tiltedly pressed condition, the central axis C is tilted relative to the substrate 32A toward the first tilting direction. The switch contact 33A is pressed by the switch pressing portion 59, and the switch contact 33A is closed. At the same time, the second protrusion 71B is in abutment with the second protrusion abutment portion 72B of the support portion 61. When the second protrusion 71B comes into abutment with the second protrusion abutment portion 72B of the support portion 61, the tilting of the on-or-off switching member 51A toward the first tilting direction is regulated. That is, the second protrusion abutment portion 72B (support portion 61) serves as a regulating portion (tilting amount regulating portion) which is configured to regulate the amount of the tilting of the on-or-off switching member 51A from the neutral condition toward the first tilting direction when the second protrusion 71B comes into abutment with the second protrusion abutment portion 72B.

In the tilting toward the first tilting direction, the supporting axis B that intersects at right angles with the central axis C in the bar portion 58 serves as the tilting center. Thus, the switch pressing portion 59 does not move to a great degree toward the second tilting direction from the neutral condition. Therefore, the switch pressing portion 59 does not move to a great degree toward the second tilting direction from the neutral condition, which ensures that the switch contact 33A is pressed by the switch pressing portion 59 in the first tiltedly pressed condition. This ensures that the switch contact 33A is turned on in the first tiltedly pressed condition.

When the second protrusion 71B comes into abutment with the second protrusion abutment portion 72B, reaction against the press force from the second protrusion 71B is applied to the on-or-off switching member 51A. Here, in the directions parallel to the central axis C, the second protrusion abutment portion 72B is located closer to the pressure receiving portion 57 than the second protrusion 71B. Thus, the reaction toward the switch contact 33A along the central axis C is applied to the on-or-off switching member 51A from the second protrusion abutment portion 72B. As a result, the hole defining portion 75 moves relative to the pin 63 toward the switch contact 33A. That is, the on-or-off switching member 51A moves toward the switch contact 33A. This further ensures that the switch contact 33A is pressed by the switch pressing portion 59, and further ensures that the switch contact 33A is turned on.

In the directions parallel to the central axis C, the bar portion 58 is coupled to the pin 63 at a position closer to the switch contact 33A than the first protrusion 71A and the second protrusion 71B. Thus, in the directions parallel to the central axis C, the position of the supporting axis B which is the center of tilting from the neutral condition is closer to the switch contact 33A. When the position of the supporting axis B is closer to the switch contact 33A, the moving amount of the switch pressing portion 59 from the neutral condition toward the second tilting direction is smaller when the switching member 51A is tilted toward the first tilting direction from the neutral condition. This, in the first tiltedly pressed condition, further ensures that the switch contact 33A is pressed by the switch pressing portion 59, and further ensures that the switch contact 33A is turned on.

On the other hand, when the on-or-off switching member 51A is tilted toward the second tilting direction from the neutral condition, the close-or-open switching member 51A is brought into a second tiltedly pressed condition as shown in FIG. 10. In the second tiltedly pressed condition, the central axis C is tilted relative to the substrate 32A toward the second tilting direction. The switch contact 33A is pressed by the switch pressing portion 59, and the switch contact 33A is turned on. At the same time, the first protrusion 71A is in abutment with the first protrusion abutment portion 72A of the support portion 61. When the first protrusion 71A comes into abutment with the first protrusion abutment portion 72A of the support portion 61, the tilting of the on-or-off switching member 51A toward the second tilting direction is regulated. That is, the first protrusion abutment portion 72A (support portion 61) serves as a regulating portion (tilting amount regulating portion) which is configured to regulate the amount of the tilting of the on-or-off switching member 51A from the neutral condition toward the second tilting direction when the first protrusion 71A comes into abutment with the first protrusion abutment portion 72A.

In the tilting toward the second tilting direction, the supporting axis B that intersects at right angles with the central axis C in the bar portion 58 serves as the tilting center. Thus, the switch pressing portion 59 does not move to a great degree toward the first tilting direction from the neutral condition. Therefore, the switch pressing portion 59 does not move to a great degree toward the first tilting direction from the neutral condition, which ensures that the switch contact 33A is pressed by the switch pressing portion 59 in the second tiltedly pressed condition. This ensures that the switch contact 33A is turned on in the second tiltedly pressed condition.

When the first protrusion 71A comes into abutment with the first protrusion abutment portion 72A, reaction against the press force from the first protrusion 71A is applied to the on-or-off switching member 51A. In the directions parallel to the central axis C, the first protrusion abutment portion 72A is located closer to the pressure receiving portion 57 than the first protrusion 71A. Thus, reaction directed toward the switch contact 33A along the central axis C is applied to the on-or-off switching member 51A from the first protrusion abutment portion 72A. As a result, the hole defining portion 75 moves relative to the pin 63 toward the switch contact 33A, and the on-or-off switching member 51A moves toward the switch contact 33A relative to the pin 63. This further ensures that the switch contact 33A is pressed by the switch pressing portion 59, and further ensures that the switch contact 33A is turned on.

In the directions parallel to the central axis C, the bar portion 58 is coupled to the pin 63 at a position closer to the switch contact 33A than the first protrusion 71A and the second protrusion 71B. Thus, in the directions parallel to the central axis C, the position of the supporting axis B which is the center of tilting from the neutral condition is closer to the switch contact 33A. When the position of the supporting axis B is closer to the switch contact 33A, the moving amount of the switch pressing portion 59 from the neutral condition toward the first tilting direction is smaller when the on-or-off switching member 51A is tilted toward the second tilting direction from the neutral condition. This, in the second tiltedly pressed condition, further ensures that the switch contact 33A is pressed by the switch pressing portion 59, and further ensures that the switch contact 33A is turned on.

Figure 11:
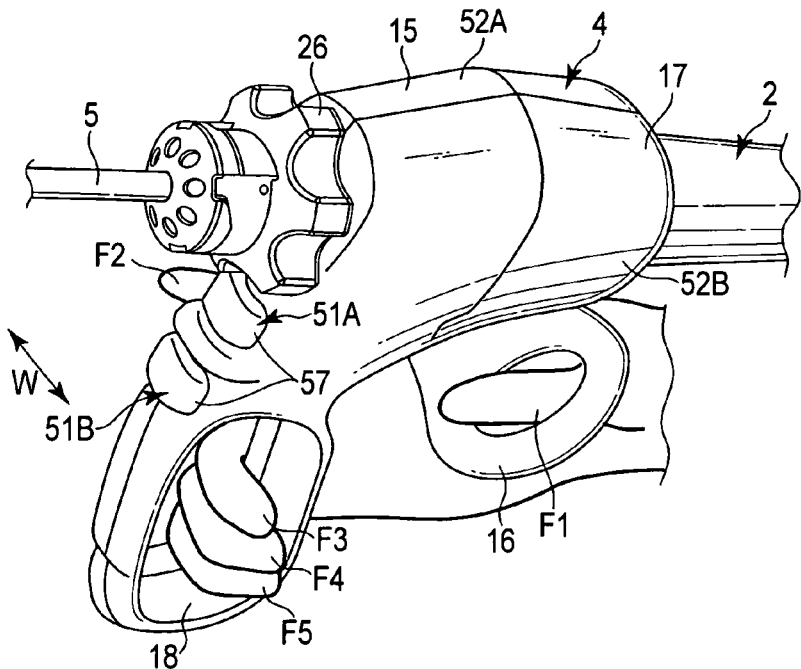
FIG. 11 is a schematic perspective view showing a state in which the handle unit is grasped according to the first embodiment.

FIG. 11 is a diagram showing a state in which the handle unit 4 is grasped. As shown in FIG. 11, when grasping the handle unit 4, the surgeon puts a middle finger F3, a ring finger F4, and a little finger F5 on the fixed handle 18, and puts a thumb F1 on the movable handle 16. The surgeon presses the pressure receiving portion 97 of the on-or-off switching member 51A or the on-or-off switching member 51B with a index finger F2, and the corresponding switch contact 33A or 33B is turned on. In this case, the movable directions of the index finger F2 is substantially perpendicular to the opening-and-closing directions of the movable handle 16, and substantially parallel to the width directions (directions of arrows W in FIG. 11) of the housing 15. Therefore, if the first tilting direction and the second tilting direction from the neutral condition correspond to the width directions of the housing 15 in each of the switching members 51A and 51B, the first tilting direction and the second tilting direction from the neutral condition correspond to the movable directions of the first finger F2 when the handle unit 4 is grasped. As a result, it is easier for the surgeon to press the pressure receiving portion 57 of each of the switching members 51A and 51B when grasping the handle unit 4.

The handle unit 4 which is the operation command transmitting device is formed when the first housing construct 52A and the second housing construct 52B are separably coupled to each other. The substrate fixing portion 35A or 35B and the support portions 61 and 62 each corresponding to the on-or-off switching member 51A or 51B are provided integrally with the first housing construct 52A, or provided to be fixed to the first housing construct 52A. The substrate 32A or 32B of each of the transmitting units 31A and 31B is provided to be fixed to the first housing construct 52A. Therefore, when the second housing construct 52B is formed, none of the substrate fixing portion 35A or 35B and the support portions 61 and 62 each corresponding to the switching member 51A or 51B need to be formed integrally with the second housing construct 52B or need to be fixed to the second housing construct 52B. The substrates 32A and 32B do not need to be fixed to the second housing construct 52B either. Therefore, the handle unit 4 is easily manufactured.

The second housing construct 52B is separable from the first housing construct 52A on the separation surface S which passes through the substrate 32A or 32B of each of the transmitting units 31A and 31B and which is perpendicular to the first tilting direction and the second tilting direction of each of the on-or-off switching members 51A and 51B. The second housing construct 52B is separable from the first housing construct 52A parallel to the first tilting direction and the second tilting direction on the separation surface S. Therefore, the substrate fixing portion 35A or 35B and the support portions 61 and 62 each corresponding to the switching member 51A or 51B are easily formed integrally with the first housing construct 52A and easily fixed to the first housing construct 52A.

Accordingly, the handle unit 4 which is the operation command transmitting device having the configuration described above provides the following advantageous effects. That is, in the handle unit 4, each of the on-or-off switching members 51A and 51B is tilted in the first tilting direction or the second tilting direction from the neutral condition around the supporting axis B that intersects at right angles with the central axis C in the bar portion 58. One of the first protrusion 71A and the second protrusion 71B provided in the bar portion 58 comes into abutment with the support portion 61 (the first protrusion abutment portion 72A or the second protrusion abutment portion 72B), so that the tilting amount of the bar portion 58 (the on-or-off switching members 51A or 51B) is regulated. Thus, when each of the on-or-off switching members 51A and 51B is tilted toward the first tilting direction, the switch pressing portion 59 does not move to a great degree toward the second tilting direction from the neutral condition. Similarly, when each of the switching members 51A and 51B is tilted toward the second tilting direction, the switch pressing portion 59 does not move to a great degree toward the first tilting direction from the neutral condition. Further, when the first protrusion 71A or the second protrusion 71B comes into abutment with the support portion 61, reaction against the press force from the first protrusion 71A or the second protrusion 71B is applied to the on-or-off switching member 51A. Thus, the hole defining portion 75 moves relative to the pin 63 toward the switch contact 33A. That is, the on-or-off switching member 51A moves toward the switch contact 33A. This, in the first tiltedly pressed condition and the second tiltedly pressed condition, ensures that the corresponding switch contact 33A or 33B is pressed by the switch pressing portion 59 of each of the on-or-off switching members 51A and 51B. This, in the first tiltedly pressed condition and the second tiltedly pressed condition, ensures that each of the switch contacts 33A and 33B is turned on.

In the present embodiment, the support portion 61 has two functions: a function of the tilting directions regulating portion which pinches the bar portion 58 so as to regulate the tilting directions of the on-or-off switching member 51, and a function of the tilting amount regulating portion which contacts the first protrusion 71A or the second protrusion 71B so as to regulate the tilting amount of the on-or-off switching member 51. However, the support portion 61 may only function as the tilting amount regulating portion which abuts on the first protrusion 71A or the second protrusion 71B and thereby regulates the tilting amount of the on-or-off switching member 51.

(Modifications)

Figure 12:
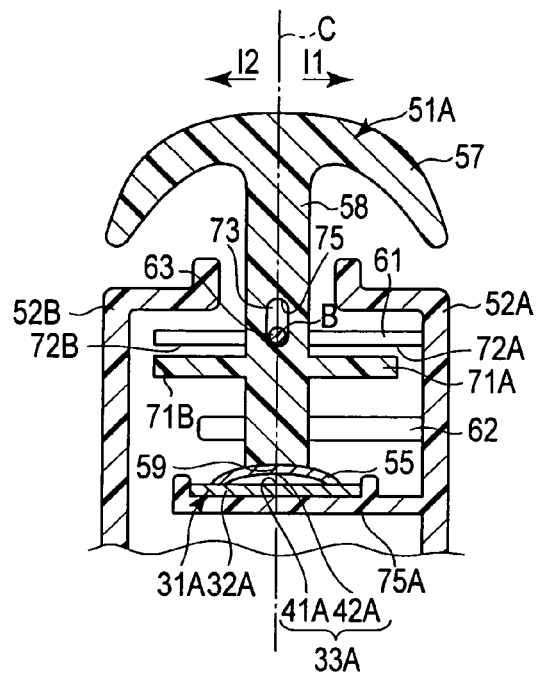
FIG. 12 is a schematic sectional view showing, in the section perpendicular to the supporting axis, the configurations of one transmitting unit, and an on-or-off switching member corresponding to the transmitting unit in the neutral condition according to a first modification.

According to the first embodiment, each of the on-or-off switching members 51A and 51B is coupled to the pin 63 which is the axis defining portion at a position of the bar portion 58 closer to the switch contact 33A than the first protrusion 71A and the second protrusion 71B. However, this is not restrictive. For example, as in a first modification shown in FIG. 12, the on-or-off switching member 51A may be coupled to the pin 63 which is the axis defining portion at a position of the bar portion 58 closer to the pressure receiving portion 57 than the first protrusion 71A and the second protrusion 71B in the directions parallel to the central axis C. In the present modification, the pin 63 is inserted through the support portion 61 and the bar portion 58. That is, the hole defining portion 75 couples the on-or-off switching member 51A to the pin 63 at a position of the bar portion 58 closer to the pressure receiving portion 57 than the first protrusion 71A and the second protrusion 71B. This also ensures that the corresponding switch contact 33A or 33B is pressed by the switch pressing portions 59 of each of the on-or-off switching members 51A and 51B in the first tiltedly pressed condition and the second tiltedly pressed condition.

Figure 13:
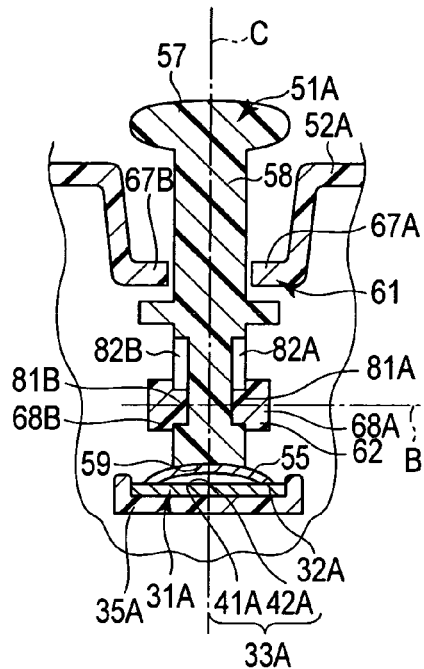
FIG. 13 is a schematic sectional view showing, in a section parallel to the supporting axis, the configurations of one transmitting unit, and an on-or-off switching member corresponding to the transmitting unit in the neutral condition according to a second modification.

According to the first embodiment, the supporting axis B is defined by the pin 63 fixed to the support portion 62 in each of the on-or-off switching members 51A and 51B. However, this is not restrictive. According to the first embodiment, in each of the on-or-off switching members 51A and 51B, the pin 63 is inserted through the hole portion 73 of the bar portion 58, so that the bar portion 58 is coupled to the pin 63 which is the axis defining portion movably along the central axis C. However, this is not restrictive. For example, as in a second modification shown in FIG. 13, in the on-or-off switching member 51A, an engaging protrusion 81A may be formed integrally with the pinch portion 68A, and an engaging protrusion 81B may be formed integrally with the pinch portion 68B, instead of the pin 63. In the present modification, the supporting axis B that intersects at right angles with the central axis C in the bar portion 58 is defined by the engaging protrusions 81A and 81B. Each of the engaging protrusions 81A and 81B projects toward the bar portion 58 in the directions parallel to the supporting point axis B. That is, the engaging protrusions 81A and 81B serve as the axis defining portion which defines the supporting axis B.

The bar portion 58 is provided with an engaging groove 82A with which the engaging protrusion 81A is engaged, and an engaging groove 82B with which the engaging protrusion 81B is engaged. The engaging grooves 82A and 82B are shaped into long grooves along the central axis C. The engaging groove 82A is movable relative to the engaging protrusion 81A along the central axis C, and the engaging groove 82B is movable relative to the engaging protrusion 81B along the central axis C. Therefore, the bar portion 58 of the on-or-off switching member 51A is coupled to the engaging protrusions 81A and 815 so that the close-or-open switching member 51A is movable relative to the engaging protrusions 81A and 81B along the central axis C. That is, the engaging grooves 82A and 82B serve as a coupling portion which couples the bar portion 58 of the on-or-off switching member 51A to the engaging protrusions 81A and 81B which are the axis defining portion so that the on-or-off switching member 51A is movable relative to the engaging protrusions 81A and 81B along the central axis C.

According to the first embodiment, the movable handle 16 is located to the proximal direction side of the fixed handle 18. However, this is not restrictive. For example, as in a third modification shown in FIG. 14, the pistol-type handle unit 4 in which the movable handle 16 is located to the distal direction side of the fixed handle 18 may be the operation command transmitting device. In the present modification, a switch housing portion 83 inside which the transmitting units 31A and 31B are provided is located between the cylindrical case 17 and the fixed handle 18. The switch housing portion 83 is a part of the housing 15, and is fixed with respect to the cylindrical case 17 and the fixed handle 18. The on-or-off switching members 51A and 51B are installed on the distal-direction side surface of the switch housing portion 83. The pressure receiving portion 57 of each of the on-or-off switching members 51A and 51B is located to the distal direction side of the movable handle 16.

As in the first embodiment, the opening-and-closing directions of the movable handle 16 are substantially parallel to the longitudinal axis L in the present modification. When the handle unit 4 is grasped, the pressure receiving portion 57 of the on-or-off switching member 51A or the on-or-off switching member 51B is pressed by the first finger F2. For example, when the on-or-off switching member 51A is pressed, the movable directions of the first finger F2 are substantially perpendicular to the opening-and-closing directions of the movable handle 16, and substantially parallel to the width directions (directions perpendicular to the sheet in FIG. 14) of the housing 15. Therefore, if the first tilting direction and the second tilting direction from the neutral condition correspond to the width directions of the housing 15 in each of the switching members 51A and 51B, the first tilting direction and the second tilting direction from the neutral condition coincide with the movable directions of the first finger F2 when the housing 15 is grasped.

As in a fourth modification shown in FIG. 15, the opening-and-closing directions of the movable handle 16 may be substantially perpendicular to the longitudinal axis L. In the present modification, the fixed handle 18 is located an opposite side with respect to the movable handle 16 across the longitudinal axis L. The opening-and-closing directions of the movable handle 16 are also substantially perpendicular to the width directions (directions of arrows W in FIG. 15) of the housing 15.

Figure 16:
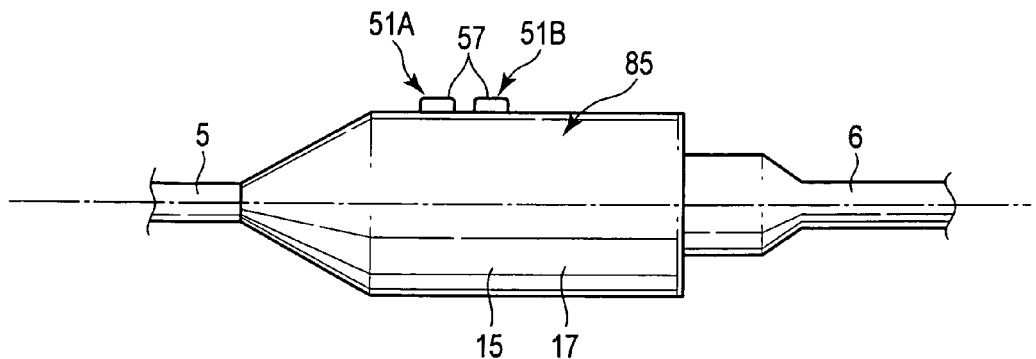
FIG. 16 is a schematic diagram showing the configuration of a holding unit according to a fifth modification.

As in a fifth modification shown in FIG. 16, a cylindrical holding unit 85 which is not provided with the fixed handle 18 and the movable handle 16 may be the operation command transmitting device. In the present modification, the housing 15 only includes the cylindrical case 17. One end of the cable 6 is connected to a proximal portion of the cylindrical case 17. The on-or-off switching members 51A and 51B are installed on the outer peripheral portion of the cylindrical case 17.

According to the first embodiment, ultrasonic vibrations are generated by the transmission of an operation command from the transmitting unit 31A, and a high-frequency current is output by the transmission of an operation command from the transmitting unit 31B. However, this is not restrictive. For example, as in a certain modification, a liquid may be supplied by the transmission of an operation command from the transmitting unit 31A, and suction may be performed by the transmission of an operation command from the transmitting unit 31B.

According to the first embodiment, the housing 15 is separable into the first housing construct 52A and the second housing construct 52B. However, this is not restrictive. For example, as in a certain modification, the cylindrical case 17 and the fixed handle 18 may be integrally formed by a single member.

The number of the transmitting units 31A and 31B and the number of the on-or-off switching members 51A and 51B are not limited to two. That is, one or more transmitting units (31A, 31B) and the same number of the on-or-off switching members (51A, 51B) as the transmitting units (31A, 31B) have only to be provided.

Therefore, according to the modifications described above, in the operation command transmitting device (4, 85), the axis defining portion (63, 81A, 81B) has only to be provided inside the housing 15, integrally with the housing 15, or to be fixed with respect to the housing 15. The supporting axis B which is parallel to the substrate (32A, 32B) of the transmitting unit (31A, 31B) and which intersects at right angles with the central axis C of the on-or-off switching member (51A, 51B) in the bar portion 58 has only to be defined by the axis defining portion (63, 81A, 81B).

In the operation command transmitting device (4, 85), the support portion 62 has only to be provided inside the housing 15, integrally with the housing 15, or to be fixed with respect to the housing 15. The support portion 62 has only to support the on-or-off switching member (51A, 51B) so that the on-or-off switching member (51A, 51B) is allowed to be tilted about the supporting axis B in the tilting directions (the first tilting direction and the second tilting direction) perpendicular to the central axis C and perpendicular to the supporting axis B from the neutral condition in which the central axis C is perpendicular to the substrate (32A, 32B) of the transmitting unit (31A, 31B).

In the operation command transmitting device (4, 85), the coupling portion (75, 82A, 82B) which couples the bar portion 58 of the on-or-off switching member (51A, 51B) to the axis defining portion (63, 81A, 81B) has only to be provided. The bar portion 58 has only to be coupled to the axis defining portion (63, 81A, 81B) by the coupling portion (75, 82A, 82B) so that the on-or-off switching member (51A, 51B) is movable relative to the axis defining portion (63, 81A, 81B) along the central axis C.

In the operation command transmitting device (4, 85), the protrusion (the first protrusion 71A, the second protrusion 71B) has only to be provided integrally with the on-or-off switching member (51A, 51B) or to be fixed with respect to the on-or-off switching member (51A, 51B). The protrusion (71A, 71B) has only to project from the bar portion 58 toward one of the tilting directions (the first tilting direction or the second tilting direction). In accordance with the protrusion (71A, 71B), the support portion 61 has only to be provided inside the housing 15, integrally with the housing 15, or to be fixed with respect to the housing 15. Thus, when the on-or-off switching member (51A, 51B) is tilted from the neutral condition, the protrusion (71A, 71B) comes into abutment with the regulating portion (72A, 72B) of the support portion 61, and the amount of the tilting of the on-or-off switching member (51A, 51B) from the neutral condition is regulated.

Reference Examples

Figure 17:
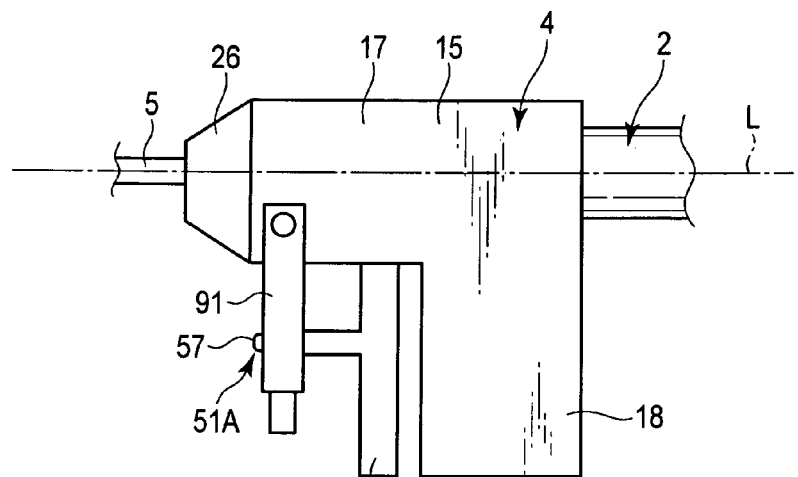
FIG. 17 is a schematic diagram showing the configuration of the handle unit according to a first reference example when a movable handle is maximally opened.
Figure 18:
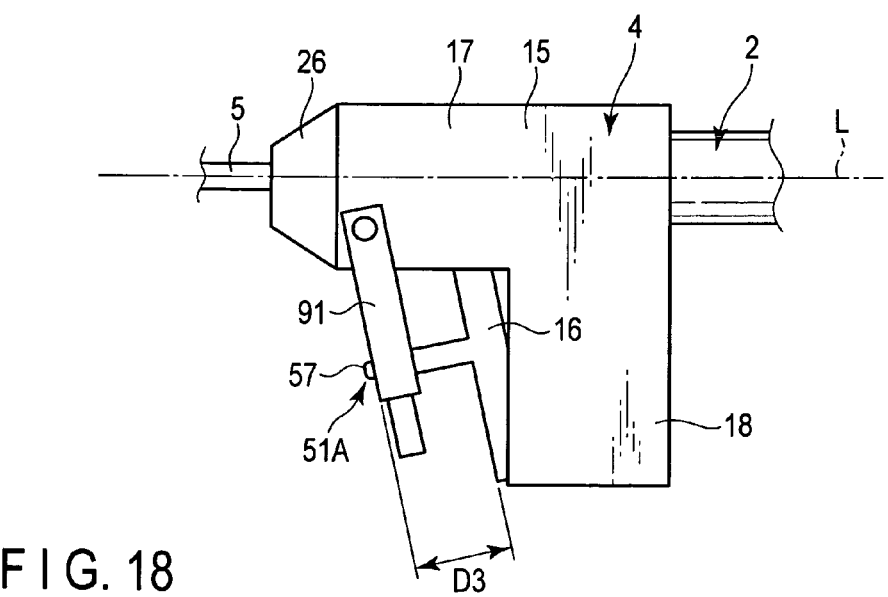
FIG. 18 is a schematic diagram showing the configuration of the handle unit according to the first reference example when the movable handle is maximally closed.

A pistol-type handle unit 4 is shown as a first reference example in FIG. 17 and FIG. 18. In the present reference example, the movable handle 16 is located to the distal direction side of the fixed handle 18, and the closing direction of the movable handle 16 substantially corresponds to the proximal direction. A movable member 91 is provided to the distal direction side of the movable handle 16 so that the movable member 91 is coupled to the movable handle 16. The on-or-off switching member 51A is installed on the distal-direction side surface of the movable member 91. The transmitting unit 31A including the switch contact 33A is provided inside the movable member 91. In the present reference example, the application direction of the press force applied to the pressure receiving portion 57 of the on-or-off switching member 51A substantially corresponds to the closing direction of the movable handle 16.

The movable member 91 is opened or closed relative to the fixed handle 18 together with the movable handle 16. Thus, as shown in FIG. 18, when the movable handle 16 is closed relative to the fixed handle 18, the on-or-off switching member 51A also moves in accordance with the movable handle 16. Thus, when the movable handle 16 is maximally closed relative to the fixed handle 18, a dimension D3 between the movable handle 16 and the on-or-off switching member 51A is not increased in directions parallel to the longitudinal axis L. Therefore, even when the handle unit 4 is grasped while the movable handle 16 is maximally closed relative to the fixed handle 18, the finger (F2) of the surgeon easily reaches the pressure receiving portion 57 of the on-or-off switching member 51A, and the pressure receiving portion 57 is easy to press.

Another pistol-type handle unit 4 is shown as a second reference example in FIG. 19 to FIG. 21. In the present reference example, the movable member 91 which is opened or closed relative to the fixed handle 18 together with the movable handle 16 is provided as in the first reference example. The on-or-off switching member 51A is installed on the distal-direction side surface of the movable member 91. The transmitting unit 31A including the switch contact 33A is provided inside the movable member 91. The application direction of the press force applied to the pressure receiving portion 57 of the on-or-off switching member 51A substantially corresponds to the closing direction of the movable handle 16. However, in the present reference example, a stopper 92 which is configured to regulate the movement of the movable member 91 toward the closing direction is provided, in contrast with the first reference example.

When the movable handle 16 is closed from a condition in which the movable handle 16 is opened relative to the fixed handle 18, the movable member 91 is closed together with the movable handle 16 until the movable member 91 abuts on the stopper 92 as shown in FIG. 20. The movement of the movable member 91 toward the closing direction is regulated when the movable member 91 abuts on the stopper 92. The movable member 91 alone can abut on the stopper 92, and the movable handle 16 does not abut on the stopper 92. Therefore, while the movable member 91 is in abutment with the stopper 92, the movable handle 16 alone moves toward the closing direction by the closing of the movable handle 16 as shown in FIG. 21.

According to the configuration described above, in the present reference example, even if press force is applied to the pressure receiving portion 57 of the on-or-off switching member 51A, the movable member 91 is not moved by the press force while the movable member 91 is in abutment with the stopper 92. Therefore, the movement of the movable handle 16 toward the closing direction caused by the press force applied to the pressure receiving portion 97 is effectively prevented, and the operability of the movable handle 16 is improved. The movable handle 16 is closed relative to the fixed handle 18 until the movable member 91 abuts on the stopper 92, so that the on-or-off switching member 51A also moves in accordance with the movable handle 16. When the movable handle 16 is maximally closed relative to the fixed handle 18, a dimension D4 between the movable handle 16 and the on-or-off switching member 51A is not increased in the directions parallel to the longitudinal axis L. Therefore, even when the handle unit 4 is grasped while the movable handle 16 is maximally closed relative to the fixed handle 18, the finger (F2) of the surgeon easily reaches the pressure receiving portion 57 of the on-or-off switching member 51A, and the pressure receiving portion 57 is easy to press.

Another pistol-type handle unit 4 is shown as a third reference example in FIG. 22. In the present reference example, the on-or-off switching member 51A is installed in the movable handle 16. The transmitting unit 31A including the switch contact 33A is provided inside the movable handle 16. However, in the present reference example, the on-or-off switching member 51A is installed on the side surface of the movable handle 16. Thus, the application direction of the press force applied to the pressure receiving portion 57 of the on-or-off switching member 51A is substantially perpendicular to the closing direction of the movable handle 16, and is different from the closing direction of the movable handle 16.

In the present reference example, the application direction of the press force applied to the pressure receiving portion 57 of the on-or-off switching member 51A is different from the closing direction of the movable handle 16. Thus, the movable handle 16 is not moved toward the closing direction by the press force even if press force is applied to the pressure receiving portion 57 of the on-or-off switching member 51A. Therefore, the movement of the movable handle 16 toward the closing direction caused by the press force applied to the pressure receiving portion 97 is effectively prevented, and the operability of the movable handle 16 is improved.

Other characteristic technical matters according to the present invention are additionally set forth below.

Notes (Additional Note 1)

An operation command transmitting device comprising:

a graspable housing;

a transmitting unit which includes a substrate provided inside the housing to be fixed with respect to the housing, and a switch contact provided on the substrate, the transmitting unit being configured to transmit a signal indicating an operation command when the switch contact is turned on;

an on-or-off switching member which includes a pressure receiving portion pressably provided outside the housing, and a bar portion extending from the pressure receiving portion toward the switch contact along a central axis, the bar portion including a switch pressing portion which is configured to press the switch contact and thereby configured to turn on the switch contact when press force is applied to the pressure receiving portion;

an axis defining portion which is provided inside the housing, integrally with the housing, or to be fixed with respect to the housing, and which defines a supporting axis parallel to the substrate and intersecting at right angles with the central axis of the on-or-off switching member in the bar portion;

a support portion which is provided inside the housing, integrally with the housing, or to be fixed with respect to the housing, and which is configured to support the on-or-off switching member so that the on-or-off switching member is allowed to be tilted around the supporting axis in tilting directions perpendicular to the central axis and perpendicular to the supporting axis from a neutral condition in which the central axis is perpendicular to the substrate;

a coupling portion which couples the bar portion of the on-or-off switching member to the axis defining portion so that the on-or-off switching member is movable relative to the axis defining portion along the central axis;

a protrusion which is provided integrally with the on-or-off switching member or provided to be fixed with respect to the on-or-off switching member, and which projects from the bar portion toward one of the tilting directions; and a regulating portion provided inside the housing, integrally with the housing, or to be fixed with respect to the housing, the protrusion being configured to come into abutment with the regulating portion when the on-or-off switching member is tilted from the neutral condition, the regulating portion is configured to regulate an amount of the tilting of the on-or-off switching member from the neutral condition, the regulating portion being located closer to the pressure receiving portion than the protrusion in directions parallel to the central axis, the regulating portion being configured to move the on-or-off switching member toward the switch contact along the central axis by reaction against a press force from the protrusion when the protrusion comes into abutment with the regulating portion.

(Additional Note 2)

The operation command transmitting device according to additional note 1, wherein the coupling portion couples the bar portion of the on-or-off switching member to the axis defining portion at a position closer to the switch contact than the protrusion in the directions parallel to the central axis.

(Additional Note 3)

The operation command transmitting device according to additional note 1, wherein the support portion includes a pinch portion which is configured to pinch the bar portion from both sides in directions parallel to the supporting point axis.

(Additional Note 4)

The operation command transmitting device according to additional note 1, wherein the housing includes a first housing construct, and a second housing construct coupled to the first housing construct separably from the first housing construct, the axis defining portion, the support portion, and the regulating portion are provided integrally with the first housing construct, or provided to be fixed with respect to the first housing construct, the substrate of the transmitting unit is provided to be fixed with respect to the first housing construct, and the second housing construct is separable from the first housing construct parallel to the tilting directions on a separation surface which passes through the substrate of the transmitting unit and which is perpendicular to the tilting directions.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An operation command transmitting device comprising:
a graspable housing;
a switch contact attached to the housing;
a pressure receiving portion pressably provided outside the housing;
a bar portion extending from the pressure receiving portion toward the switch contact along a central axis, the bar portion being movable relative to the housing along the central axis, the bar portion being able to tilt relative to the housing from an untilted neutral condition;
a switch pressing portion which is provided in an opposite side part of the pressure receiving portion in the bar portion, and which is configured to press the switch contact in accordance with each of a movement of the bar portion along the central axis and a tilting motion of the bar portion;

an axis defining portion which is provided integrally with the housing or provided to be fixed with respect to the housing, and which defines a supporting axis passing through the bar portion, the bar portion being configured to be tilted around the supporting axis, a position of the supporting axis relative to the housing being configured to be maintained regardless of the movement of the bar portion along the central axis and the tilting motion of the bar portion;

an abutment portion provided integrally with the housing or provided to be fixed with respect to the housing, the bar portion being configured to come into abutment with the abutment portion when the bar portion is tilted from the untilted neutral condition; and a coupling portion which is provided to the bar portion, and which is coupled to the axis defining portion while the bar portion is movable along the central axis and is allowed to be tilted around the supporting axis.

2. The operation command transmitting device according to claim 1, wherein the bar portion includes a protrusion which projects toward one of the tilting directions of the bar portion, and which is configured to come into abutment with the abutment portion when the bar portion is tilted from the neutral condition, and the abutment portion is configured to regulate a tilting amount of the bar portion so that the tilting ting amount from the neutral condition is not greater than a predetermined tilting amount when the protrusion comes into abutment with the abutment portion.

3. The operation command transmitting device according to claim 2, wherein the abutment portion is located closer to the pressure receiving portion than the protrusion in directions parallel to the central axis, and the abutment portion is configured to move the bar portion toward the switch contact along the central axis by reaction against a press force from the protrusion when the protrusion comes into abutment with the abutment portion.

4. The operation command transmitting device according to claim 1, wherein the axis defining portion includes a pin which is provided to be fixed with respect to the housing, and in which a pin shaft is coaxial with the supporting axis, and the coupling portion includes a hole defining portion which defines a hole portion, and which is movable relative to the pin along the central axis, the hole portion passing through the bar portion in directions parallel to the supporting axis, the pin being inserted through the hole portion.

5. The operation command transmitting device according to claim 1, wherein the housing includes a first housing construct, and a second housing construct coupled to the first housing construct separably from the first housing construct, the axis defining portion and the abutment portion are provided integrally with the first housing construct, or provided to be fixed with respect to the first housing construct, and the switch contact is provided to be fixed with respect to the first housing construct.

6. The operation command transmitting device according to claim 1, wherein the housing includes a fixed handle, and a movable handle configured to be opened or closed relative to the fixed handle, and the tilting directions of the bar portion correspond to the width directions of the housing perpendicular to the opening-and-closing directions of the movable handle.

7. An operation command transmitting device comprising:
a graspable housing;
a switch contact provided to be fixed with respect to the housing;
a pressure receiving portion pressably provided outside the housing;
a bar portion extending from the pressure receiving portion toward the switch contact;
a switch pressing portion which is provided in an opposite side part of the pressure receiving portion in the bar portion, and which can press the switch contact;
an axis defining portion which couples the bar portion to the housing so that the bar portion is allowed to be tilted around a supporting axis which passes through the bar portion;
an abutment portion provided integrally with the housing or provided to be fixed with respect to the housing, the bar portion being configured to come into abutment with the abutment portion when the bar portion is tilted from an untilted neutral condition; and
a coupling portion which is provided to the bar portion, and which is coupled to the axis defining portion while the bar portion is movable along a central axis of the bar portion and is allowed to be tilted around the supporting axis,
wherein the bar portion includes a protrusion which projects toward one of the tilting directions of the bar portion, and which is configured to come into abutment with the abutment portion when the bar portion is tilted from the neutral condition, and
wherein the abutment portion is configured to regulate a tilting amount of the bar portion so that the tilting amount from the neutral condition is not greater than a predetermined tilting amount when the protrusion comes into abutment with the abutment portion, and
wherein the abutment portion is located closer to the pressure receiving portion than the protrusion in directions parallel to the central axis, and the abutment portion is configured to move the bar portion toward the switch contact along the central axis by reaction against a press force from the protrusion when the protrusion comes into abutment with the abutment portion.

* * * * *